United States Patent
Markandey

Patent Number: 5,517,580
Date of Patent: May 14, 1996

[54] METHOD FOR ESTIMATING THE SHAPE OF AN OBJECT FROM IR IMAGE SHADING

[75] Inventor: Vishal Markandey, Dallas, Tex.

[73] Assignee: Texas Insturments Incorporated, Dallas, Tex.

[21] Appl. No.: 91,463

[22] Filed: Jul. 13, 1993

Related U.S. Application Data

[63] Continuation of Ser. No. 717,434, Jun. 19, 1991, abandoned.

[51] Int. Cl.$^6$ ................................................. H04N 5/33
[52] U.S. Cl. .................................... 382/203; 348/164
[58] Field of Search ............................. 382/1, 8, 25, 28, 382/41, 58, 100, 154, 203, 206, 312; 358/113, 109, 88; 250/330, 340, 342; 348/144, 164

[56] References Cited

U.S. PATENT DOCUMENTS

| | | | |
|---|---|---|---|
| 4,110,617 | 8/1978 | Legille | 358/113 |
| 5,168,161 | 12/1992 | Markandey | 250/330 |

OTHER PUBLICATIONS

Zheng et al "Estimation of Illuminant Direction, Albedo and Shape from Shading", IEEE 1991.
Frankot et al. "A Method for Enforcing Integrability in Shape from Shading Algorithms" IEEE. Trans. Patt. Anal. Machine Int. vol. 10, No. 4 Jul. 1988 pp. 439–451.
Zheng et al. "Estimation of Illuminant Direction, Albedo, and Shape from Shading", IEEE Trans. Patt. Anal. Machine Int. vol. 13, No. 7, Jul. 1991, pp. 680–697.
Choe et al. "3–D Shape from a Shaded and Textural Surface Image", IEEE Trans. Patt. Anal. Machine. Int., vol. 13, No. 9, Sep. 1991 pp. 907–919.

*Primary Examiner*—Joseph Mancuso
*Assistant Examiner*—Larry J. Prikockis
*Attorney, Agent, or Firm*—Robert L. Troike; Leo N. Heiting; Richard L. Donaldson

[57] ABSTRACT

A method for estimating the shape of a body that emits electromagnetic energy using a sensor (10) having an image plane (15) and the ability to measure the intensity of the electromagnetic radiation (12) received at a point on image plane (15) comprises the steps of first expressing the intensity of radiation (12) reaching image plane (15) as a function of surface gradient parameters (p,q) for a pre-determined point ($P_i$) on object (14). Next, the method requires measuring the intensity (E(s,t)) of radiation (12) that sensor (10) senses at the point ($P_i$) on image plane (15). The method then requires determining the values of the surface gradient parameters (p,q) for the point ($P_i$) on object (14) that minimizes the difference between the expressed intensity ($F_1$(p,q)) for the pre-determined point ($P_i$) on object (14) and the measured intensity (E(s,t)) at pixel ($p_i$) on image plane (15).

13 Claims, 2 Drawing Sheets

METHOD FOR ESTIMATING THE SHAPE OF AN OBJECT FROM IR IMAGE SHADING

This application is a Continuation of application Ser. No. 07/717,434, filed Jun. 19, 1991, now abandoned.

TECHNICAL FIELD OF THE INVENTION

This invention relates in general to electromagnetic radiation sensing and analysis, and more particularly to a method, based on image shading, for estimating the shape of a three-dimensional object that emits electromagnetic radiation.

BACKGROUND OF THE INVENTION

For a variety of sensing applications, it is important to determine the shape of sensed objects that emit electromagnetic radiation. For example, in passive ranging applications such as in obtaining a map based on infrared signatures of a terrain having hills and valleys, it is necessary to determine the elevation of the hills and the depths of the valleys. There are numerous ways of solving this problem, but the known methods for determining the height, width, and depth of hills and valleys using infrared imagery require the use of multiple sensors or multiple views with a single sensor at different points. Techniques that determine shape from image shading are available for visible imagery. There is a need, however, for a similar technique using infrared imagery, because of the importance of infrared imagery in defense applications.

For example, with known methods if an infrared image is to be used to determine the shape of a three-dimensional object, it is necessary either to have two sensors for two separate infrared images of the particular object at the same time, or to take a first image at one point and a second image at another point with the same infrared sensor. With these two images, computer correlation of the images is possible. The computer correlation permits an analysis and determination of the shape of the particular object.

The principal limitation associated with this correlation approach is that it requires extensive computer processing. Additionally, this stereo sensor approach either requires the precise operation of two separate sensors or, alternatively, requires a longer flying period or viewing time to obtain the different positions necessary for multiple image orientations. The two sensor solution poses a more complicated correlation problem than the single sensor solution. However, in a hostile environment, such as when an aircraft must assess a potential target, the increased viewing time for the second infrared image with the same sensor often increases the risk of attack for the viewing aircraft.

While there are methods that use a single sensor to estimate the shape of a target that reflects electromagnetic radiation, these methods determine the shape of a three-dimensional object that reflects electromagnetic radiation reflected radiation may include light waves, millimeter waves, or microwaves that go to the three dimensional object and bounce from its surface. An example of a method of this type may be seen in, B. K. P. Horn, *Robot Vision*, The MIT Press, Cambridge, Mass., (1986), which presents a technique for estimating the shape of a three-dimensional object from shading using television imagery. For the situation where the object only emits instead of reflecting electromagnetic radiation such as in infrared emission, the laws of physics are different. Consequently, it is not possible to use the same approach to determine the surface shape of the object.

Thus there is a need for a method and system that permits shape estimation from electromagnetic radiation emitted from three-dimensional objects.

There is a need for an improved method of shape estimation for military and other uses that overcomes the problem of having to use stereo cameras or stereo camera images and thereby the need for more extensive computing capability and the need for greater periods of time to record the image of the emitted radiation.

Moreover, there is the need for a method and system that can establish the shape of an object that emits infrared radiation, and does not rely on the laws of physics appropriate only for the reflection electromagnetic radiation.

SUMMARY OF THE INVENTION

In accordance with the present invention, a method for estimating the shape of an object from an image of its electromagnetic radiation, and in particular, infrared emission, is provided which substantially eliminates and overcomes the disadvantages and problems associated with prior shape estimation methods.

Accordingly, for a body that emits electromagnetic energy in the direction of an image plane of sensor that measures the intensity of electromagnetic radiation at points on the image plane the present invention provides an estimate of the object's shape. In essence, the method comprises the steps of expressing the intensity of the radiation that emits from the object to reach the sensor image plane as a function of the surface gradient parameters for a predetermined point on the object. The next step is to measure the intensity of the radiation that the sensor senses at a corresponding point on the image plane. Then, the method determines the values of the surface gradient parameters for the predetermined point on the object that minimize the difference between the intensity of the radiation that the sensor senses at the image plane point and the expressed intensity of the radiation that reached the sensor image plane. With an increasing number of predetermined object points, an increasing number of object point gradients are defined by the method. From the set of surface gradients corresponding to the object points, the shape of the body results.

A technical advantage of the present invention is that it provides a way to estimate the shape of a three-dimensional object that emits infrared radiation while the sensor remains at only one position.

Another technical advantage of the present invention is that it, eliminates the need for more than one sensor or more than one sensor aspect to obtain an estimate of the surface shape of the body that emits infrared radiation. Not having to correlate two or more images may significantly reduces the amount of computer processing time necessary to obtain an estimate of the surface shape of an object.

Yet another technical advantage of the present invention is that it does not depend on reflection, but only on emission, of electromagnetic radiation, an important consideration in many defense scenarios where there is no natural electromagnetic radiation reflection (night time) and the need for covert operation precludes the possibility of reflecting artificial electromagnetic radiation.

BRIEF DESCRIPTION OF THE DRAWINGS

For a more complete understanding of the present invention and the advantages thereof, reference is now made to the following detailed description taken in conjunction with the accompanying FIGURES in which.

DETAILED DESCRIPTION OF THE INVENTION

The preferred embodiment of the present invention is best understood by referring to FIGS. 1 through 4 of the drawings, like numerals being used for like and corresponding parts of the various drawings.

Figure 1:
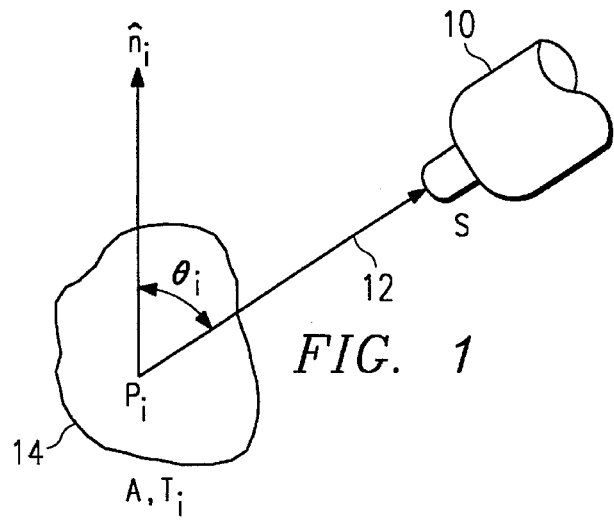
FIG. 1 provides a conceptual view of the environment for practicing method of the present invention.

FIG. 1 illustrates application of the preferred embodiment of the present invention in which sensor 10 receives electromagnetic radiation, in particular for the preferred embodiment infrared emissions, 12 from three-dimensional body 14. Considering the point $P_i$ on surface patch A having a temperature $T_i$, let $\hat{n}_i$ be the surface normal at $P_i$ and let $\theta_i$ be the angle between $\hat{n}_i$ and the view direction of sensor 10. For the configuration of FIG. 1, the total radiation $J_i$ for a wavelength $\lambda$ emitted by point $P_i$ may be calculated according to the following black-body radiation formula:

$$J_i = \frac{\epsilon C_1}{\lambda^5 [e^{(C_2/\lambda T_i)} - 1]}, \tag{1}$$

where $\epsilon$ is the surface emissivity, with a value close to 0.9 for most natural objects at infrared wavelengths of 8–12 μm, and $C_1$ and $C_2$ are universal constants such that $C_1 = 3.742 \times 10^8$ W·μm/m², and $C_2 = 1.439 \times 10^4$ μm·K.

Equation (1) gives the relationship between the total radiation, the wavelength $\lambda$ and temperature $T_i$ of object 14 at the point $P_i$. From Equation (1) which provides the total radiation emitted by point $P_i$, it is possible to determine the fraction of the radiation that reached sensor 10. Equation (2) provides this relationship:

$$R_{is} = J_i \tau_{\lambda R} \cos \theta_i \tag{2}$$

where $\tau_{\lambda R}$ is the atmospheric attenuation for wavelength $\lambda$ at range R. The value of $\tau_{\lambda R}$ be determined from standard LOWTRAN codes. Thus, this gives a value for the radiation that sensor 10 intercepts.

Using Equation (2) it is possible to use $\theta_i$ to estimate the orientation of surface patch $A_i$ at point $P_i$. To do this, surface A may be expressed as a function $Z(X,Y)$ for which the surface gradient (p,q) may be represented according to the following Equation (3):

$$(p,q) = \left( \frac{\partial Z}{\partial X}, \frac{\partial Z}{\partial Y} \right). \tag{3}$$

Then, assuming that the view vector from $P_i$ to the sensor 10 is $(0,0,1)^T$, the surface normal $\hat{n}_i$ may be expressed as follows:

$$\hat{n}_i = \frac{(-p, -q, -1)^T}{\sqrt{1 + p^2 + q^2}} \text{ for which} \tag{4}$$

$$\cos \theta_i = \frac{1}{\sqrt{1 + p^2 + q^2}}.$$

Combining Equations (1), (2), and (4) provides an expression representing the fraction of the total radiation that reaches sensor 10 as follows:

$$R_{is} = \frac{1}{\sqrt{1 + p^2 + q^2}} \cdot \frac{\epsilon C_1 \tau_{\lambda R}}{\lambda^5 [e^{(C_2/\lambda T_i)} - 1]} \tag{5}$$

As a result, it is possible to obtain an expression for the radiation that reaches sensor 10 in terms of the gradients for surface A of object 14.

At this point, it is appropriate to examine the image that sensor 10 measures. Consider that point $P_i$ projects to a pixel $p_i$ in the image plane of sensor 10. Suppose further that the image intensity at the image plane point $p_i$ is $E(s,t)$ where (s,t) are image plane coordinates for the image plane of sensor 10. In other words, $E(s,t)$ is the gray-scale value for the image that sensor 10 measures from object 14. With the measure of image intensity $E(s,t)$ it is possible to establish the relationship between the fraction of the total radiation reaching sensor 10 and the image intensity that sensor 10 measures according to the following Equation (6):

$$K_a E(s,t) + K_b = R_{is}, \tag{6}$$

where $K_a$ and $K_b$ are sensor calibration constants. (See, N. Nandhakumar & J. K. Aggarwal, "Integrated Analysis of Thermal and Visual Images for Scene Interpretation," IEEE Transactions on Pattern Analysis and Machine Intelligence, 10(4):469–81 (1988).) Equation (6) may be rewritten more generally as the following equation:

$$E(s,t) = F_1(p,q) \tag{7}$$

With a view to Equation (7), and for application of the preferred embodiment, it is necessary to understand that the only parameters to which the user typically has access only are the image intensities of sensor 10 along with the appropriate calibration parameters $K_a$ and $K_b$. If it is possible to determine the image intensity at point $p_i$, the next step is to obtain values for p and q which represent the surface gradient for surface A at $P_i$. Thus, for a known temperature $T_i$, it is possible to determine the value for the surface gradients for area A.

The following discussion explains a preferred method for obtaining these values, but first transforms the Gaussian space into stereographic space and establishes coordinates (f,g) as stereographic equivalents of the Gaussian coordinates (p,q).

Figure 2:
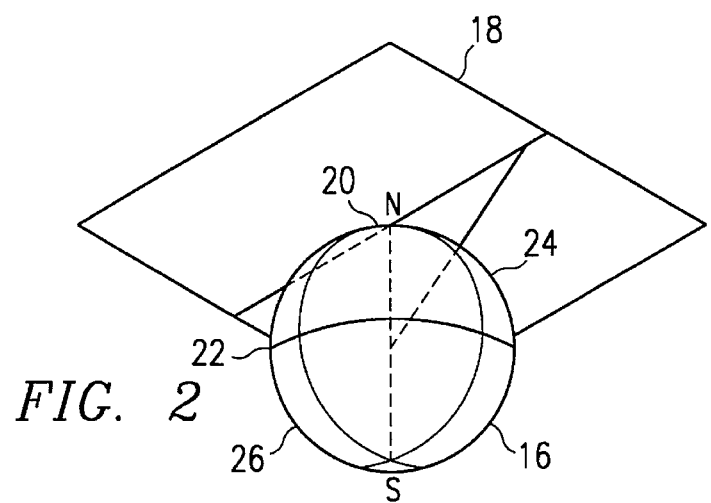
FIG. 2 illustrates the relationship between the Gaussian sphere and the gradient space of the object in FIG. 1.
Figure 3:
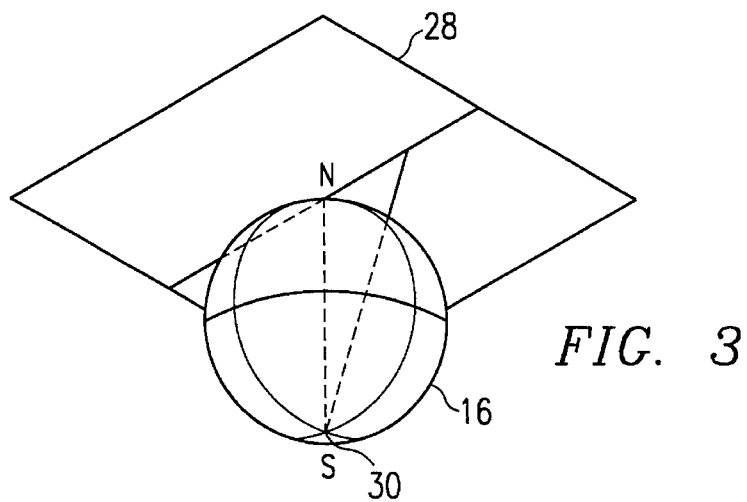
FIG. 3 shows a stereographic projection of the gradient space for the preferred embodiment.

FIGS. 2 and 3 illustrate the reasoning for transforming the surface gradient (p,q) into stereographic space to obtain coordinates (f,g). Surface orientation may be represented by the gradient (p,q) or the unit normal $\hat{n}_i$ to $P_i$. The Gaussian sphere represents all possible surface orientations. FIG. 2 shows the relationship between the Gaussian sphere and the gradient space. It can be seen that only the "northern" half of sphere 16 projects onto plane 18, with the equator 20 of the sphere projecting to infinity. This means that there will be an ambiguity between projections obtained from the "northern" 22 and "southern" 24 parts of sphere 16. Additionally, there will be problems for orientations corresponding to the sphere 16 equator 22 as these points project to infinity. FIG. 3 shows the stereographic projection 24 of sphere 16 in stereographic space. It may be seen that all points on sphere 16 project uniquely to finite locations in plane 24, with the exception of "south pole" 26. For a detailed explanation, see B. K. P. Horn, *Robot Vision*, the MIT Press Cambridge, Mass. (1986).

The following Equation (8) establishes the relationship between stereographic coordinates (f,g) and the gradient space coordinates (p, q) as follows:

$$f = \frac{2p}{1 + \sqrt{1 + p^2 + q^2}}, \quad g = \frac{2q}{1 + \sqrt{1 + p^2 + q^2}} \quad (8)$$

In stereographic coordinates, Equation (7) may now be rewritten in the following general form:

$$E(s,t) = F_2(f,g) \quad (9)$$

where $F_2(f,g)$ is the stereographic equivalent of $F_1(p,q)$. To obtain values of f and g that satisfy Equation (9), it is appropriate to construct a minimization problem such that the function to be minimized combines the constraint of Equation (9) with a term representing the spatial smoothness of surface A of object 14. In this construction we may define a constraint error term $e_c$ to represent an expression for the difference between the left-hand and right-hand sides of equation 9 for varying values of f and g as shown in Equation 10 as follows:

$$e_c = \iint [E(s,t) - F_2(f,g)]^2 ds\, dt \quad (10)$$

Additionally, the error term associated with the spatial smoothness of surface A may be represented as the following Equation (11):

$$e_s = \iint [f_s^2 + f_t^2 + g_s^2 + g_t^2] ds\, dt \quad (11)$$

where $$f_s = \frac{\partial f}{\partial s}, \; f_t = \frac{\partial f}{\partial t}, \; g_s = \frac{\partial g}{\partial s}, \; \text{and } g_t = \frac{\partial g}{\partial t}.$$

With this characterization of the error terms $e_c$ and $e_s$, the solution of Equation (9) requires values for (f,g) that minimize the overall error term:

$$e = e_s + \omega e_c \quad (12)$$

The error term $e_s$ accounts for the fact that surface area A may not be smooth over the region of integration. Therefore, Equation (12) provides a measure of how much E(s,t) varies from the constraint of Equation (9). By minimizing Equation (12), an optimal solution for f and g and, therefore, p and q are obtained. The variable $\omega$, as it appears in Equation (12) is a weighting factor that applies to the constraint error of Equation (10) to weight the relative contributions of the terms $e_s$ and $e_c$. The constant, $\omega$, may be varied according to the particular application and parameters associated with the measurement of e. Solving for Equation (12) may be done iteratively to obtain the solutions of the following Equations (13) and (14)

The iterative solution obtained for this problem is:

$$f_{ki}^{n+1} = \bar{f}_{ki}^n + w[E_{ki} - F_2(f_{ki}^n, g_{ki}^n)] \frac{\partial F_2}{\partial f} \quad (13)$$

$$g_{ki}^{n+1} = \bar{g}_{ki}^n + w[E_{ki} - F_2(f_{ki}^n, g_{ki}^n)] \frac{\partial F_2}{\partial g} \quad (14)$$

where n is the number of iterations, and the quantities under bars are local neighborhood averages of the values within the neighborhood of the pixel having the coordinates (s,t). From Equation (8), the resulting values for f and g may be used to obtain values for the gradient space coordinate (p,q) as follows:

$$p = \frac{4f}{4 - f^2 - g^2}, \quad q = \frac{4g}{4 - f^2 - g^2} \quad (15)$$

The iterative solutions of equations (13) and (14) will give progressively smaller values for e in equation (12). Thus, as a result of the values for p and q there is a unique vector associated with each pixel on the image plane of sensor 10. This vector represents the surface gradient of surface $A_l$ at point $P_l$. Consequently, for all of the pixels on the image plane of sensor 10, there is a combined or complete estimation of the surface $A_l$ for object 14.

In summary, the preferred embodiment of the present invention provides a method for estimating the shape of an object from infrared shading of the object at the image plane of an infrared sensor. The process requires first determining the fraction of the total radiation that reaches the image plane of the sensor. Next, the measurement of the image intensity at the pixel points on the image plane of the sensor is determined. Upon relating the image intensity for the pixel points on the image plane to the fraction of the total radiation reaching the particular pixel point as a function of the surface gradients for the object, it is possible to construct a set of error terms. By iteratively minimizing the error terms, the present invention provides a method to obtain values of the surface gradients for the object at unique points relating to each of the pixels on the sensor image plane. The surface gradients, when taken collectively, define the surface shape estimate.

Figure 4:
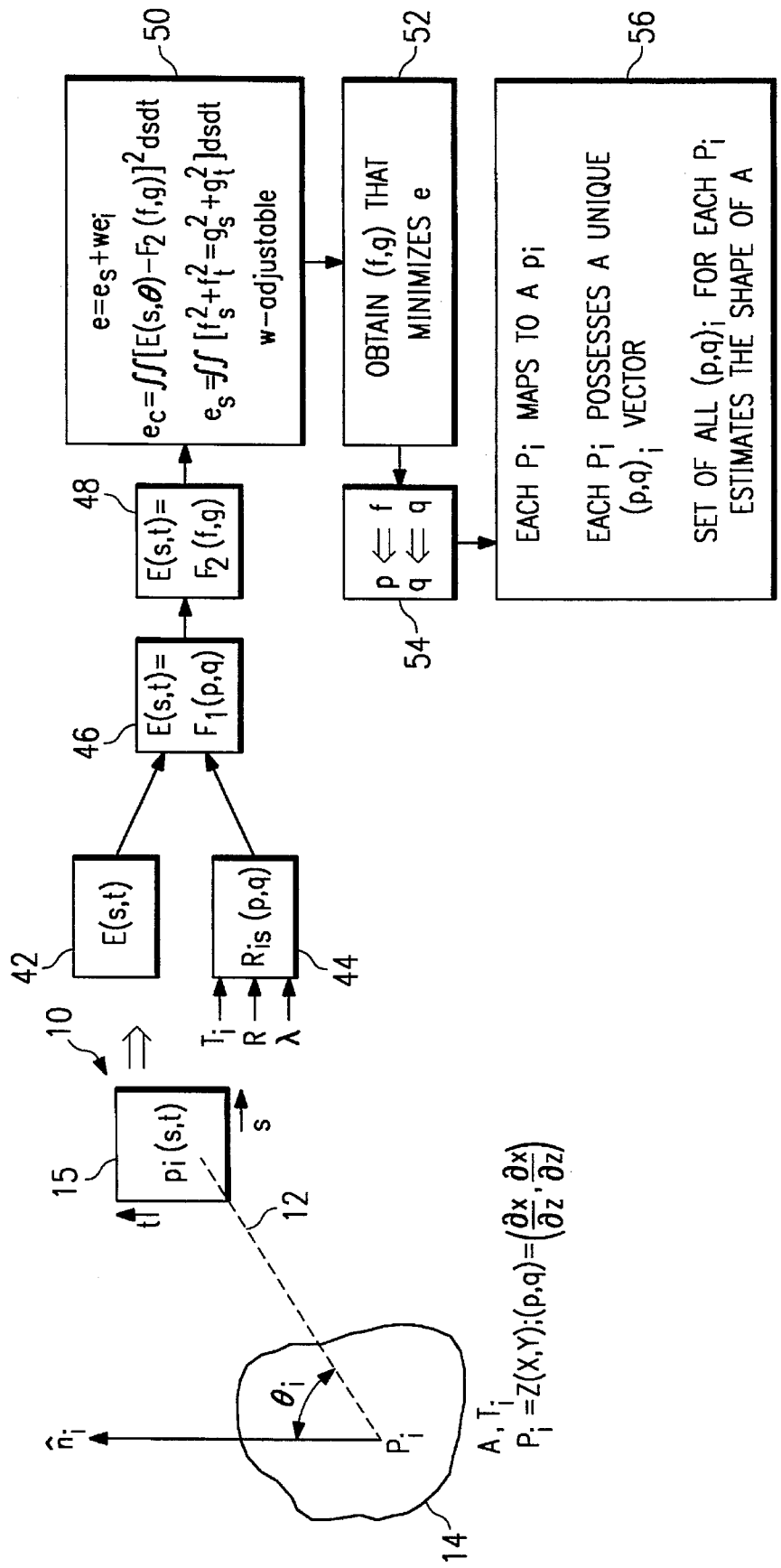
FIG. 4 provides a functional block diagram of the preferred embodiment.

FIG. 4 illustrates a block diagram of an exemplary circuit that uses the method of preferred embodiment. Sensor 10 receives at $p_i$ of image plane 15 infrared radiation that point $p_i$ of surface A on body 14 emits. The pixel $p_i$ has the coordinates (s,t) on image plane 15. Circuitry 42 associated with sensor 10 to translate the value of radiation 12 at $p_i$ to intensity value E(s,t). At the same time, values for temperature $T_i$, range R, and wavelength λ may be input into circuit 44 to calculate a value for the fraction of the total radiation $R_{is}$ as a function of the surface gradient (p,q) at point $P_i$ of surface A. In circuit 46, the function $F_1(p,q)$ is constrained to the value of the image intensity E(s,t) from circuit 42. Circuit 48 translates p and q from the Gaussian coordinate system to a stereographic coordinate system to create function $F_2(f,g)$ and constrains $F_2(f,g)$ to the image value E(s,t).

From circuit 48, circuit 50 establishes the error relationship of equation (12). Circuit 52 iteratively obtains values for f and g to minimize the error term e. This results in optimal values for f and g which circuit 54 translates back into Gaussian coordinate systems terms p and q for the surface gradient of area A at point $P_l$. To completely estimate surface area A across all points $P_l$, circuit 56 relates each pixel $p_i$ to a point $P_l$ and assigns a unique $P_i$ value of (p,q) vector. The set of all (p,q) for each $P_i$ on area A, provides a complete estimation for the surface A.

The circuits supporting the system of FIG. 4 may be a combination of hardware and software and may operate on a variety of processors. Alternatively, the circuit of FIG. 4 may simply be embedded within sensor 10 to provide a complete mapping of the surface area estimate from object 14.

Although the present invention and its advantages have been described in detail, it should be understood that various changes, substitutions and alterations may be made herein without departing from the spirit and scope of the invention as defined in the appended claims.

What is claimed is:

1. A method for estimating the shape of a body emitting electromagnetic energy, comprising the steps of:

sensing, by a sensor having an image plane, the intensity of electromagnetic energy emitted by predetermined points on the body received at corresponding points on said image plane;

expressing said intensity of said emitted electromagnetic energy received at said corresponding points on said image plane as a function of surface gradient parameters for predetermined points on the body;

measuring said intensity of said emitted electromagnetic energy sensed by said sensor at said corresponding points on said image plane; and determining values of said surface gradient parameters for said predetermined points on the body that minimize the difference between the expressed intensity for said predetermined points on the body and the measured intensity at said corresponding points on the image plane to estimate the shape of the body.

2. The method of claim 1, wherein said electromagnetic energy comprises infrared radiation emitted from the body.

3. The method of claim 1, wherein said expressing step comprises the step of relating said predetermined point on the body to a unique pixel point on the image plane and constraining said sensed intensity on said sensor image plane point to equal a function of the surface gradient parameters for said predetermined point on the body.

4. The method of claim 3, further comprising the step of translating said function of surface gradient parameters for said predetermined point on a body into a function whose parameters are stereographic components from a stereographic component system.

5. The method of claim 3, further comprising the step of constructing an error term for the error arising by constraining said image plane point intensity to equal the intensity of the fraction of the total radiation reaching the point on the image plane and the variation of the body surface from a smooth surface.

6. The method of claim 5, further comprising the step of iteratively determining the surface gradient values for the body by minimizing said error term.

7. The method of claim 6, further comprising the step of translating said stereographic coordinate system gradient values to the Gaussian equivalent to characterize the surface shape of the body.

8. The method of claim 1, further comprising the step of characterizing the surface of said body by a plurality of surface gradient parameters associated with a plurality of points on the image plane.

9. A circuit for estimating the shape of an object that emits infrared radiation comprising:

a sensor having an image plane, said image plane comprising a plurality of pixels;

circuitry coupled to said sensor for measuring the intensity of the emitted infrared radiation received at each of said pixels;

circuitry for relating the intensity of radiation reaching each of said pixels as a function of the surface gradient of an associated point on the object; and circuitry for determining the surface gradient of a plurality of points associated with each of said pixels as a function of the difference between the intensity measured at each of said pixel points on said image plane and the intensity of said radiation reaching said pixel point as a function of said surface gradients; and circuitry for consolidating each of said surface gradients associated with each of said points on said surface and constructing therefrom an estimate of the shape of said surface.

10. The circuit of claim 9, further comprising circuitry for determining the fraction of said infrared radiation as a function of the surface gradients of said object.

11. The circuit of claim 9, further comprising circuitry for constraining the measured intensity of said plurality of pixels to a function of said surface gradients.

12. The circuit of claim 10, further comprising circuitry for determining and minimizing the error between the measured intensity of said plurality of pixels and said function of said surface gradients so as to obtain a value of said surface gradients.

13. A system for estimating the shape of an object that emits infrared radiation, the system comprising:

a sensor having an image plane, said image plane comprising a plurality of pixels;

means, coupled to said sensor, for measuring the intensity of the emitted infrared radiation received at each of said pixels;

means for relating the intensity of radiation reaching each of said pixels as a function of the surface gradient of an associated point on the object; and means for determining the surface gradient of a plurality of points associated with each of said pixels as a function of the difference between the intensity measured at each of said pixel points on said image plane and the intensity of said radiation reaching said pixel point as a function of said surface gradients; and means for consolidating each of said surface gradients associated with each of said points on said surface and constructing therefrom an estimate of the shape of said surface.

* * * * *